US012171286B2

(12) United States Patent
Woods

(10) Patent No.: US 12,171,286 B2
(45) Date of Patent: Dec. 24, 2024

(54) TACTILE DEVICE FOR GARMENT

(71) Applicant: The Gap, Inc., Albuquerque, NM (US)

(72) Inventor: Tamara Woods, Davis, CA (US)

(73) Assignee: The Gap, Inc., San Francisco, CA (US)

( * ) Notice: Subject to any disclaimer, the term of this patent is extended or adjusted under 35 U.S.C. 154(b) by 0 days.

(21) Appl. No.: 17/506,231

(22) Filed: Oct. 20, 2021

(65) Prior Publication Data

US 2022/0117337 A1 Apr. 21, 2022

Related U.S. Application Data

(60) Provisional application No. 63/094,204, filed on Oct. 20, 2020.

(51) Int. Cl.
*A41D 27/20* (2006.01)
*A41D 27/24* (2006.01)

(52) U.S. Cl.
CPC ............. *A41D 27/20* (2013.01); *A41D 27/24* (2013.01)

(58) Field of Classification Search
CPC .. A41D 2400/32; A41D 27/20; A41D 27/205; A41D 27/22; A41D 13/0012; A41D 11/00; A44C 17/02; A44C 25/00; A44C 3/008; G09B 1/14; A15F 5/022
USPC .......................................................... 2/253
See application file for complete search history.

(56) References Cited

U.S. PATENT DOCUMENTS

| 240,841 | A | * | 5/1881 | Paul ....................... | A41D 27/20 2/248 |
|---|---|---|---|---|---|
| 464,916 | A | * | 12/1891 | Taylor ..................... | A41B 9/08 450/95 |
| 849,164 | A | * | 4/1907 | Roede ................... | A44C 11/002 63/38 |
| 2,078,461 | A | * | 4/1937 | Siegel .................. | A41D 27/201 2/93 |

(Continued)

OTHER PUBLICATIONS

Johnson, N., "Convex Polyhedra With Regular Faces," *Canadian Journal of Mathematics*, 1966, 18: 169-200, DOI: https://doi.org/10.4153/CJM-1966-021-8.

(Continued)

*Primary Examiner* — Heather Mangine
(74) *Attorney, Agent, or Firm* — Morgan, Lewis & Bockius LLP

(57) ABSTRACT

A garment including a pocket is provided. The pocket includes first and second surfaces, each respective surface including a corresponding distal end portion, a corresponding proximal end portion parallel to the corresponding distal end portion, a corresponding upper end portion connecting the corresponding distal end portion and the corresponding proximal end portion, and a corresponding lower end portion connecting the corresponding distal end portion and the corresponding proximal end portion. A cord includes an exterior, a first end portion interposing the corresponding proximal end portions, and a second end portion interposing the corresponding lower end portions. Each respective tactile element includes a through-hole and is disposed on the cord circumjacent to the exterior. A first seam affixes the corresponding proximal end portions and the first end portion of the cord. A second seam affixes the corresponding lower end portions and the second end portion of the cord.

25 Claims, 7 Drawing Sheets

(56) References Cited

U.S. PATENT DOCUMENTS

| | | | | |
|---|---|---|---|---|
| 2,628,452 | A * | 2/1953 | Gladstein | A63H 3/52 446/28 |
| 3,208,640 | A * | 9/1965 | Paulson | B65D 75/5822 383/7 |
| 3,308,479 | A * | 3/1967 | Sesco, Jr. | A41B 13/10 446/28 |
| 3,447,165 | A * | 6/1969 | Brosk | A41D 11/00 446/28 |
| 3,771,171 | A * | 11/1973 | Mitchell | A41D 13/0506 2/2.5 |
| 3,951,812 | A * | 4/1976 | Hsu | B01D 17/0202 73/61.61 |
| 4,123,804 | A * | 11/1978 | Michael | A41D 27/20 2/211 |
| 4,138,745 | A * | 2/1979 | Greenspan | A41D 11/00 446/28 |
| 4,334,326 | A * | 6/1982 | Mallow | A45F 5/02 2/249 |
| 4,448,579 | A * | 5/1984 | Currie | G09B 19/02 434/203 |
| 4,508,956 | A * | 4/1985 | Prichard | A43D 11/12 12/54.1 |
| 4,654,991 | A * | 4/1987 | Jones | A63H 33/40 40/124 |
| 4,670,909 | A * | 6/1987 | Forrester | A41D 19/002 2/160 |
| 4,723,323 | A * | 2/1988 | Wright, Jr. | G09B 19/0076 2/244 |
| 4,791,681 | A * | 12/1988 | Dean | A41D 13/012 2/253 |
| 5,205,747 | A * | 4/1993 | Tan | G06C 1/00 434/203 |
| 5,395,245 | A * | 3/1995 | Heinz | G09B 1/14 434/207 |
| 5,421,032 | A * | 6/1995 | Murphy | A41D 27/208 2/247 |
| 5,509,147 | A * | 4/1996 | Busquets | A41D 27/202 2/253 |
| 5,517,696 | A * | 5/1996 | Krugler | A41D 27/20 2/919 |
| 5,566,391 | A * | 10/1996 | Williamson | A41D 13/04 2/48 |
| 5,584,074 | A * | 12/1996 | Battle-Smith | A41D 27/00 2/113 |
| 5,639,005 | A * | 6/1997 | Chouinard | A45F 3/04 224/582 |
| 5,644,794 | A * | 7/1997 | Hull | A45F 5/02 2/108 |
| 5,813,584 | A * | 9/1998 | Mauser | A45F 5/00 446/28 |
| 5,829,060 | A * | 11/1998 | Falk | A41D 13/0012 2/102 |
| 5,991,925 | A * | 11/1999 | Wu | A41D 13/0012 224/931 |
| 6,148,443 | A * | 11/2000 | Maastricht | A63B 57/00 2/69 |
| 6,206,854 | B1 * | 3/2001 | Weaver | A61M 25/02 604/179 |
| 6,257,473 | B1 * | 7/2001 | Ringelstetter | E01H 1/1206 224/675 |
| 6,317,894 | B1 * | 11/2001 | Blechman | A41D 15/002 2/125 |
| 6,405,376 | B1 * | 6/2002 | Falk | A41D 31/102 2/102 |
| RE38,497 | E * | 4/2004 | Falk | A41D 13/0012 2/247 |
| 6,769,139 | B1 * | 8/2004 | Goldkind | A41D 27/20 2/247 |
| 7,073,204 | B1 * | 7/2006 | Boyles | A41D 13/1236 2/114 |
| 7,434,271 | B2 * | 10/2008 | Klayman-Grodsky | A41D 15/04 2/244 |
| 7,464,413 | B2 * | 12/2008 | Todd | A41D 27/20 2/94 |
| 7,594,281 | B1 * | 9/2009 | Stinson | A62B 17/003 2/310 |
| 7,774,859 | B2 * | 8/2010 | Murray | A41D 27/20 2/249 |
| 8,225,442 | B2 * | 7/2012 | Davis | A45C 9/00 5/655 |
| 8,402,562 | B1 * | 3/2013 | Seddiki | A41D 27/205 2/247 |
| 8,819,865 | B1 * | 9/2014 | Crye | A41D 13/02 2/2.14 |
| 9,060,555 | B1 * | 6/2015 | Harris | A41D 27/20 |
| 9,089,169 | B1 * | 7/2015 | Covo | A41D 1/04 |
| 9,557,139 | B1 * | 1/2017 | Miner | A44B 18/0073 |
| 11,173,371 | B2 * | 11/2021 | Watanabe | G06C 1/00 |
| 11,452,323 | B2 * | 9/2022 | Hourani | A41D 27/201 |
| 2001/0054192 | A1 * | 12/2001 | Haar | A42B 3/0406 2/69 |
| 2005/0177939 | A1 * | 8/2005 | Botera | A47G 9/083 5/413 R |
| 2005/0258057 | A1 * | 11/2005 | Gelphman | A45C 13/02 206/583 |
| 2006/0102676 | A1 * | 5/2006 | Gibson | A45F 3/04 224/648 |
| 2009/0100571 | A1 * | 4/2009 | Soto | A41D 27/10 2/244 |
| 2009/0205102 | A1 * | 8/2009 | Anderson | A45F 4/12 2/93 |
| 2009/0289046 | A1 * | 11/2009 | Richmond | A41D 13/0051 429/61 |
| 2010/0083422 | A1 * | 4/2010 | Lebl | A41D 27/20 2/251 |
| 2010/0281597 | A1 * | 11/2010 | Lang | A41D 1/04 2/243.1 |
| 2011/0006090 | A1 * | 1/2011 | Bollard | A45C 15/00 224/257 |
| 2011/0016615 | A1 * | 1/2011 | Massey | A41D 27/201 2/251 |
| 2011/0088138 | A1 * | 4/2011 | Chen | H05B 3/342 2/160 |
| 2011/0113524 | A1 * | 5/2011 | Sinder | A45F 3/20 224/148.1 |
| 2011/0119800 | A1 * | 5/2011 | Garrido | A41D 27/201 2/102 |
| 2012/0060256 | A1 * | 3/2012 | Parker | A41D 19/0041 2/85 |
| 2012/0167273 | A1 * | 7/2012 | Ballinger | A41D 19/0024 2/160 |
| 2012/0227153 | A1 * | 9/2012 | Laycock | A41D 27/10 2/88 |
| 2013/0277407 | A1 * | 10/2013 | Murdoch | A45F 3/04 224/639 |
| 2014/0047613 | A1 * | 2/2014 | Henderson | A63F 9/001 463/48 |
| 2014/0068832 | A1 * | 3/2014 | Jordan | A41D 1/005 2/69 |
| 2014/0101821 | A1 * | 4/2014 | Dammann | A42B 1/12 2/171.4 |
| 2015/0053735 | A1 * | 2/2015 | Murdoch | A45F 3/04 224/640 |
| 2015/0201761 | A1 * | 7/2015 | Wollenberg | A45F 4/02 224/160 |
| 2015/0273178 | A1 * | 10/2015 | Johnson | A61M 21/02 600/27 |
| 2015/0305420 | A1 * | 10/2015 | Daniels | A41D 1/02 2/93 |
| 2016/0113333 | A1 * | 4/2016 | Blauser | A62B 17/003 2/96 |
| 2016/0235146 | A1 * | 8/2016 | Kim | A41D 27/20 |
| 2016/0270554 | A1 * | 9/2016 | Silverman | A41D 27/20 |
| 2017/0014595 | A1 * | 1/2017 | Heath | G09B 1/00 |
| 2019/0059815 | A1 * | 2/2019 | Smith | A41D 27/08 |

(56) References Cited

U.S. PATENT DOCUMENTS

| | | | | |
|---|---|---|---|---|
| 2019/0060604 | A1* | 2/2019 | Smith | A41D 1/06 |
| 2019/0166798 | A9* | 6/2019 | Crane | A01K 15/026 |
| 2020/0195042 | A1* | 6/2020 | Topolosky | A41D 1/005 |
| 2020/0305581 | A1* | 10/2020 | Barklow | A41D 13/0007 |
| 2020/0348107 | A1* | 11/2020 | McFadden | F41C 33/0227 |
| 2021/0030074 | A1* | 2/2021 | Paradis | A61M 21/02 |
| 2021/0289864 | A1* | 9/2021 | Obletz | A41D 13/0012 |
| 2021/0392979 | A1* | 12/2021 | Zoll | A41F 1/002 |
| 2022/0117337 | A1* | 4/2022 | Woods | A41D 27/24 |
| 2022/0192350 | A1* | 6/2022 | Irons | A45F 5/00 |
| 2023/0284773 | A1* | 9/2023 | Popp | B65D 33/16 |
| 2023/0404182 | A1* | 12/2023 | Dammaschke | A41D 1/04 |

OTHER PUBLICATIONS

Kotschick, D., "The Topology and Combinatorics of Soccer Balls: When Mathematicians Think About Soccer Balls, the Number of Possible Designs Quickly Multiplies," *American Scientist*, 2006, 94(4):350-357.

Midha, V., et al., "An Approach to Seam Strength Prediction Using Residual Thread Strength," *Research Journal of Textile and Apparel*, 2011, 15(3):75-85.

Namiranian, R., et al., "Seam Slippage and Seam Strength Behavior of Elastic Woven Fabrics Under Static Loading," *Indian Journal of Fiber and Textile Research*, 2014, 39(3):221-229.

\* cited by examiner

TACTILE DEVICE FOR GARMENT

CROSS-REFERENCE TO RELATED APPLICATION

The present Application claims priority to U.S. Provisional Patent Application No. 63/094,204, entitled "Tactile Device for Garment," filed Oct. 20, 2020, which is hereby incorporated by reference in its entirety.

TECHNICAL FIELD

The present disclosure relates generally to garments. More particularly, the present disclosure relates to tactile devices for garments.

BACKGROUND

People are known to exhibit certain habits when experiencing specific emotions. Williams, D G, 1973, "So-called 'Nervous Habits,'" The Journal of Psychology, 83 (1), pg. 103. For instance, many people fidget with their fingers when experiencing anxiousness, attention deficit, or nervousness. Id.

One conventional solution for this is individual handheld devices. Such conventional devices have various mechanisms, such as buttons or bearings, that a user manipulates with their hand to allay feelings of anxiousness, attention deficit, or nervousness. However, each such conventional handheld device is typically larger than a conventional die, meaning an external viewer can generally see a user manipulate them. Moreover, such conventional devices are untethered to larger objects, allowing for an appreciable risk of misplacement, or even worse, children swallowing them. Yet another disadvantage of conventional devices is their unsatisfactory durability resulting in fatigue from repeated use. Moreover, conventional devices are burdensome and difficult to repair.

Given the above background, what are needed in the art are improved tactile devices that are discretely disposed in a garment. In particular, there is a need for enabling a wearer to utilize such tactile devices without the knowledge of an external observer.

SUMMARY

The present disclosure addresses the above-identified shortcomings. The present disclosure provides tactile devices that are discretely manipulated by a user with increased durability. Specifically, the tactile devices include a cord that is affixed to one or more seams of a pocket or a garment. From this, the cord is fixedly disposed within the pocket and secured such that the user can handle the cord vigorously without dislodging the cord from the one or more seams. Furthermore, a plurality of tactile elements is disposed circumjacent to the exterior surface of the cord, such that each respective tactile element in the plurality of tactile elements is strung on the cord and exposed within the pocket. Moreover, the one or more seams prevent removal of the plurality of tactile devices from the cord. By handling the cord and/or a respective tactile element, the user is provided with a tactual sensation. With the tactile device discretely disposed within an internal cavity of the pocket, the user can discretely handle the tactical device with a hand of the user in the pocket without the knowledge of an external observer. Accordingly, the tactile devices for garments of the present disclosure provide an improved sense of comfort to a wearer of a garment having the tactile device. In addition, the tactile device is affixed within the garment in a concealed and secured manner, which allows for safe operation, increased durability, and ornamentation.

One aspect of the present disclosure provides a garment including a pocket. The pocket includes a first surface and a second surface that opposes the first surface. The first surface includes a first distal end portion, a first proximal end portion running parallel or approximately parallel to the first distal end portion, a first upper end portion connecting the first distal end portion and the first proximal end portion, and a first lower end portion connecting the first distal end portion and the first proximal end portion. The second surface includes a second distal end portion, a second proximal end portion running parallel or approximately parallel to the second distal end portion, a second upper end portion connecting the second distal end portion and the second proximal end portion, and a second lower end portion connecting the second distal end portion and the second proximal end portion. The garment includes a cord. The cord includes an exterior surface, a first end portion disposed interposing between the first proximal end portion and the second proximal end portion, and a second end portion disposed interposing between the first lower end portion and the second lower end portion. The garment further includes a plurality of tactile elements. Each respective tactile element in the plurality of tactile elements includes a through-hole. Moreover, each respective tactile element is disposed on the cord circumjacent to the exterior surface of the cord. A first seam affixes the first proximal end portion, the second proximal end portion, and the first end portion of the cord. A second seam affixes the first lower end portion, the second lower end portion, and the second end portion of the cord. From this, the cord is fixedly disposed within the pocket.

In some embodiments, the garment further includes a third seam affixing the first upper end portion and the second upper end portion. From this, an aperture forms that is configured for receiving a hand of the subject.

In some embodiments, the first seam is characterized by a first seam strength in between 20 kilograms-force (kgf) and 35 kgf. In some embodiments, the second seam is characterized by a second seam strength between 15 kgf to 30 kgf.

In some embodiments, a first length of the cord exposed in the pocket by the first seam and the second seam is between 2 inches and 3 inches. In some embodiments, a second length that is a sum of each length of each respective tactile element in the plurality of tactile elements is in a range of from 1.5 inches to 1.9 inches.

In some embodiments, the plurality of tactile elements includes one or more subsets of tactile elements. In some embodiments, each respective tactile element in each respective subset of tactile elements is characterized by a unique shape of the respective subset of tactile elements.

In some embodiments, the one or more subsets of tactile elements includes at least two tactile elements. Each tactile element in a first subset of tactile in the one or more subsets of tactile elements is characterized by a first unique shape. Moreover, each tactile element in a second subset of tactile elements in the one or more subsets of tactile elements is characterized by a second unique shape.

In some embodiments, the first unique shape is prism shape. The prism shape includes a first base including a first opening of a corresponding through-hole of the respective tactile element, a second base including a second opening of the corresponding through-hole of the respective tactile element, and a plurality of surface faces interposing between the first base and the second base.

In some embodiments, the plurality of surface faces includes a first subset of faces in the plurality of surface faces. Each respective face in the first subset of faces includes one or more protrusions of a first shape. In some embodiments, the plurality of surface faces includes a second subset of faces in the plurality of surface faces. Each respective face in the second subset of faces includes one or more protrusions of a second shape.

In some embodiments, a first face in the first subset of faces is parallel to a second face in the first subset of faces, and a third face in the second subset of faces is parallel to a fourth face in the second subset of faces.

In some embodiments, a first diameter of the first opening is in a range of from 1.5 millimeters (mm) to 2.0 mm. Moreover, in some embodiments, a second diameter of the second opening is in a range of from 5.2 mm to 5.7 mm.

In some embodiments, a transition region interposing between the first opening and the second opening of the corresponding through-hole includes a step transition from the first diameter of the first opening to the second diameter of the second opening. In some embodiments, the transition region interposing between the first opening and the second opening of the corresponding through-hole includes a ramp transition from the first diameter of the first opening to the second diameter of the second opening.

In some embodiments, the one or more subsets of tactile elements includes at least three tactile elements. Each tactile element in a first subset of tactile elements in the one or more subsets of tactile elements is characterized by a spheroid shape. Moreover, each tactile element in a second subset of tactile elements in the one or more subsets of tactile elements is characterized by a toroidal shape. Furthermore, each tactile element in a third subset of tactile elements in the one or more subsets of tactile elements is characterized by a prism shape. The prism shape includes a first base including a first opening of a corresponding through-hole of the respective tactile element, a second base including a second opening of the corresponding through-hole of the respective tactile element, and a plurality of surface faces interposing between the first base and the second base.

In some embodiments, the first subset of tactile elements includes a first tactile element and a second tactile element in the plurality of tactile elements. The second subset of tactile elements includes a third tactile element and a fourth tactile in the plurality of tactile elements. Moreover, the third subset of tactile elements includes a fifth tactile element in the plurality of tactile elements.

In some embodiments, the fifth tactile element is disposed on the cord interposing between the third tactile element and the fourth tactile element.

In some embodiments, each tactile element in the plurality of tactile elements includes thermoplastic rubber.

In some embodiments, the first unique shape is spheroid shaped. In some embodiments, the first unique shape is spheroid with a plurality of dimples. In some embodiments, each dimple in the plurality of dimples includes a third diameter.

In some embodiments, the first unique shape is a toroidal shape.

In some embodiments, the garment is selected from the group consisting of: a jacket, a sweatshirt, a sweater, an outerwear, a pair of pants, and a pair of shorts.

In some embodiments, the plurality of tactile elements is between 3 tactile elements and 11 tactile elements. In some embodiments, the cord is a bungee cord.

In some embodiments, the cord is made of cotton, wool, jute, leather, polyester, nylon or a blend thereof. In some embodiments, the first seam or the second seam is formed using an International Organization for Standardization (IOS, 1991) class 100 single-thread chain stitch, class 200 hand stitch, class 300 lockstitch, class 400 multi-thread stitch, class 500 overedge/overlock stitch, or class 600 covering chain stitch.

In some embodiments, the first seam or the second seam is a U.S. Standard SS superimposed seam, LS lapped seam, BS bound seam, or FS flat seam.

Additional aspects and advantages of the present disclosure will become readily apparent to those skilled in this art from the following detailed description, where only illustrative embodiments of the present disclosure are shown and described. As will be realized, the present disclosure is capable of other and different embodiments, and its several details are capable of modifications in various obvious respects, all without departing from the disclosure. Accordingly, the drawings and description are to be regarded as illustrative in nature, and not as restrictive.

BRIEF DESCRIPTION OF THE DRAWINGS

The embodiments disclosed herein are illustrated by way of example, and not by way of limitation, in the figures of the accompanying drawings. Like reference numerals refer to corresponding parts throughout the drawings.

DESCRIPTION OF EMBODIMENTS

Figure 1:
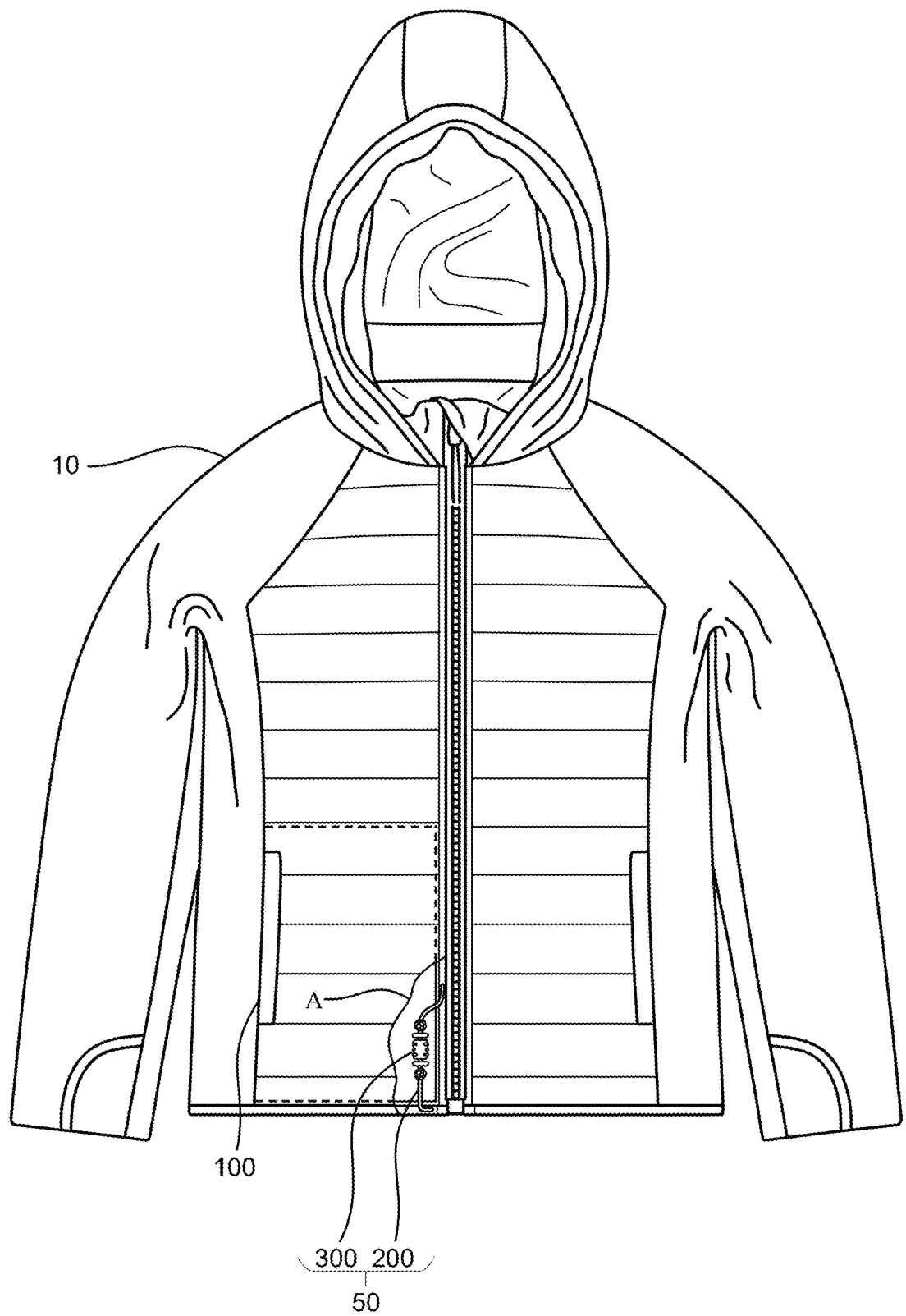
FIG. 1 illustrates a view of a garment having a pocket including a tactile device, in accordance with an exemplary embodiment of the present disclosure.

Reference will now be made in detail to embodiments, examples of which are illustrated in the accompanying drawings. In the following detailed description, numerous specific details are set forth in order to provide a thorough understanding of the present disclosure. However, it will be apparent to one of ordinary skill in the art that the present disclosure may be practiced without these specific details. In other instances, well-known methods, procedures, components, circuits, and networks have not been described in detail so as not to unnecessarily obscure aspects of the embodiments.

Plural instances may be provided for components, operations or structures described herein as a single instance. Finally, boundaries between various components are some-what arbitrary, and particular operations are illustrated in the context of specific illustrative configurations. Other forms of functionality are envisioned and may fall within the scope of the implementation(s). In general, structures and functionality presented as separate components in the example configurations may be implemented as a combined structure or component. Similarly, structures and functionality presented as a single component may be implemented as separate components. These and other variations, modifications, additions, and improvements fall within the scope of the implementation(s).

It will also be understood that, although the terms "first," "second," etc. may be used herein to describe various elements, these elements should not be limited by these terms. These terms are only used to distinguish one element from another. For example, a first tactile element could be termed a second tactile element, and, similarly, a second tactile element could be termed a first tactile element, without departing from the scope of the present disclosure. The first tactile element and the second tactile element are both tactile elements, but they are not the same tactile element.

The terminology used herein is for the purpose of describing particular embodiments only and is not intended to be limiting of the claims. As used in the description of the embodiments and the appended claims, the singular forms "a," "an," and "the" are intended to include the plural forms as well, unless the context clearly indicates otherwise. It will also be understood that the term "and/or" as used herein refers to and encompasses any and all possible combinations of one or more of the associated listed items. It will be further understood that the terms "comprises" and/or "comprising," when used in this specification, specify the presence of stated features, integers, steps, operations, elements, and/or components, but do not preclude the presence or addition of one or more other features, integers, steps, operations, elements, components, and/or groups thereof.

The foregoing description, for purpose of explanation, has been described with reference to specific embodiments. However, the illustrative discussions below are not intended to be exhaustive or to limit the embodiments to the precise forms disclosed. Many modifications and variations are possible in view of the above teachings. The embodiments are chosen and described in order to best explain the principles and their practical applications, to thereby enable others skilled in the art to best utilize the embodiments and various embodiments with various modifications as are suited to the particular use contemplated.

In the interest of clarity, not all of the routine features of the embodiments described herein are shown and described. It will be appreciated that, in the development of any such actual implementation, numerous implementation-specific decisions are made in order to achieve the designer's specific goals, such as compliance with use case- and business-related constraints, and that these specific goals will vary from one implementation to another and from one designer to another. Moreover, it will be appreciated that such a design effort might be complex and time-consuming, but nevertheless be a routine undertaking of engineering for those of ordering skill in the art having the benefit of the present disclosure.

As used herein, the term "about" or "approximately" can mean within an acceptable error range for the particular value as determined by one of ordinary skill in the art, which can depend in part on how the value is measured or determined, e.g., the limitations of the measurement system. For example, "about" can mean within 1 or more than 1 standard deviation, per the practice in the art. "About" can mean a range of +20%, +10%, +5%, or +1% of a given value. Where particular values are described in the application and claims, unless otherwise stated, the term "about" means within an acceptable error range for the particular value. The term "about" can have the meaning as commonly understood by one of ordinary skill in the art. The term "about" can refer to +10%. The term "about" can refer to +5%.

As used herein, the term "fabric" means a material used in the construction of the present disclosure. Fabrics include natural fibers (e.g., cotton, hemp, flax, fur, jute, linen, silk, wool, etc.) and/or synthetic fibers (e.g. latex, nylon, polyester, polyurethane, rayon, rubber, silicon, spandex, etc.), or a blend thereof. Additionally, these fabrics may have any suitable weave used in the art (e.g. twill weave, plain weave, satin weave, etc.), or have any suitable bonding or felting used in the art. Moreover, unless expressly stated otherwise, the term "fabric" includes general materials used in productions of garments such as elastics, metals, and plastics.

In addition, as used herein, the term "right" means a right hand side with respect to a perspective of a wearer of a garment of the present disclosure. Similarly, as used herein, the term "left" means a left hand side with respect to the perspective of the wearer of the garment of the present disclosure.

For convenience in explanation and accurate definition in the appended claims, the terms "upper," "lower," "up," "down," "upwards," "downwards," "laterally," "longitudinally," "inner," "outer," "inside," "outside," "inwardly," "outwardly," "interior," "exterior," "front," "rear," "back," "forwards," and "backwards" are used to describe features of the exemplary embodiments with reference to the positions of such features as displayed in the figures.

Furthermore, when a reference number is given an "$i^{th}$" denotation, the reference number refers to a generic component, set, or embodiment. For instance, a tactile element termed "tactile element i" refers to the $i^{th}$ tactile element in a plurality of tactile elements.

Figure 2:
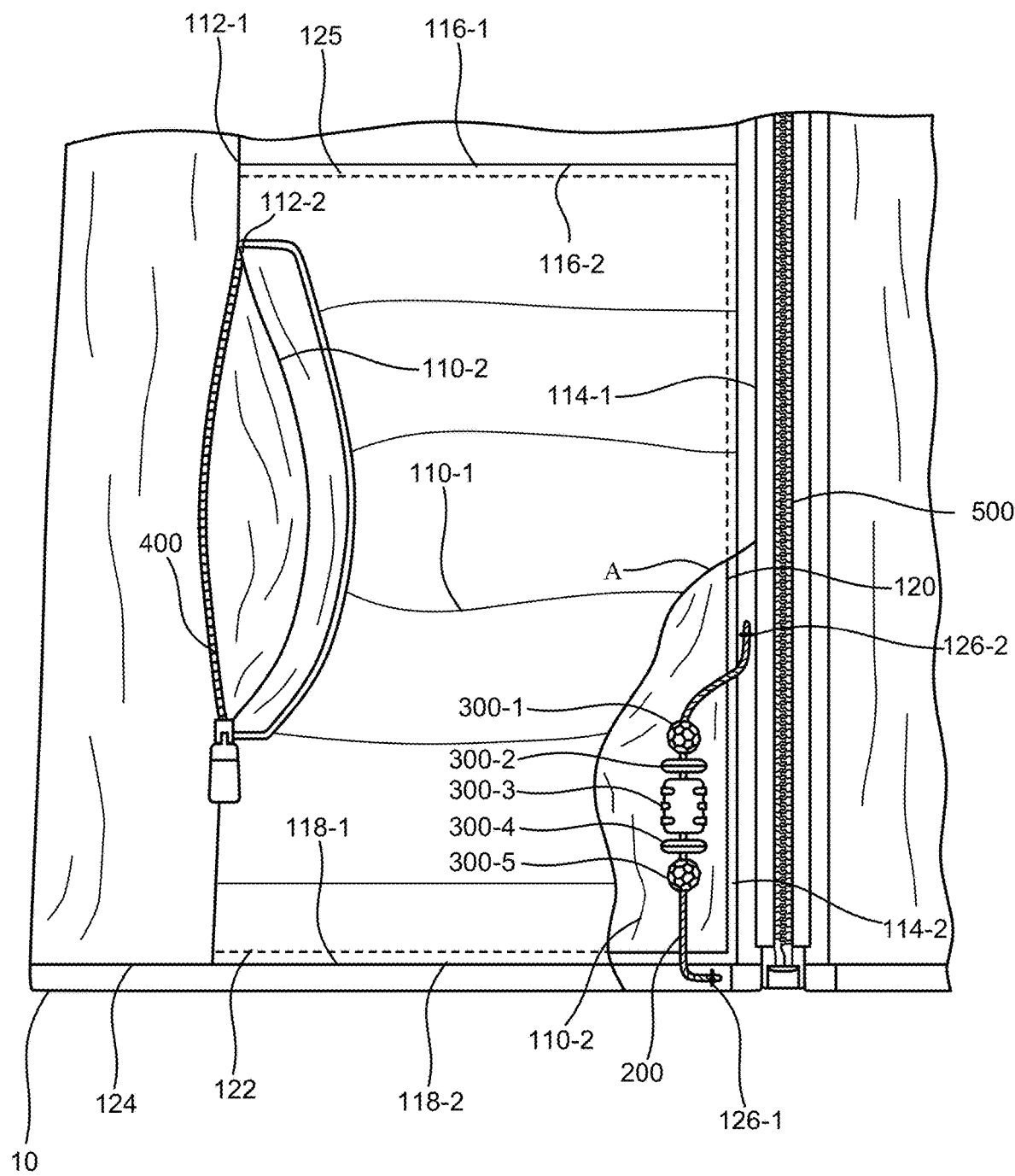
FIG. 2 illustrates a view of a pocket including a tactile device, in accordance with an exemplary embodiment of the present disclosure.

Referring to FIG. 1 and FIG. 2, a garment 10 is illustrated in accordance with an embodiment of the present disclosure. In some embodiments, the present disclosure provides a variety of tactile devices (e.g., tactile device 50 of FIG. 1) for use on a garment 10. In some embodiments, the tactile devices 50 of the present disclosure may be integrally combined with an article of clothing (e.g., a garment, an accessory, etc.), for example, a pair of pants, a pair of shorts, a suit, a jacket, a sweatshirt (e.g., garment 10 of FIG. 1), an outerwear, a swimsuit, a blouse, a dress, a shirt, etc. By integrally combining the tactile device 50 with the garment 10, the durability of the tactile device 50 greatly improves and allows a user to handle the tactile device 50 vigorously without separating the tactile device 50 from the garment 10.

In some embodiments, the garment 10 includes a pocket (e.g., pocket 100 of FIG. 2). In some embodiments, the pocket 100 includes a first surface (e.g., first surface 110-1 of FIG. 2) and a second surface (e.g., second surface 110-2 of FIG. 2) that opposes the first surface 110-1. In some embodiments, the first surface 110-1 is an exterior surface of the garment 10, such that the first surface 110-1 is visible to a wearer of the garment 10 or exterior observer of the garment 10. By way of example, in some embodiments, the first surface 110-1 forms an exterior portion of the garment 10 and the second surface 100-2 forms an interior portion of the garment 10. However, the present disclosure is not limited thereto. In some embodiments, the first surface 110-1 and the second surface 110-2 are formed from a first pattern of fabric, such as a base fabric of the garment 10. As used herein, the "base fabric" refers to a fabric from which one or more corresponding portions of the garment 10 is made. For instance, in some embodiments, a portion along an edge of a pattern cut from the base fabric is used to form the first surface 110-1 of the garment 10. In some embodiments, an exterior fabric layer of the first surface 110-1 is integral or continuous with the base fabric of the garment 10, rather than being a separate piece of fabric. However, the present disclosure is not limited thereto. In some embodiments, the base fabric and/or the exterior fabric layer is made from natural and/or synthetic fibers including cotton, wool, flax, polyester, blends thereof, and the like that may have a suitable textile weave used in the art. In some embodiments, the base fabric and/or the exterior fabric layer is made entirely or primarily of natural fibers (e.g., cotton, wool, flax, etc.) rather than synthetic fibers. Additional details and information regarding the materials and design of textiles is described in Sinclair, Rose, ed., 2014, "Textiles and Fashion: Materials, Design and Technology." Elsevier, print, which is hereby incorporated by reference in its entirety. As shown in FIG. 1 and FIG. 2, a line A denotes a boundary region of an exterior view of the first surface 110-1 of the pocket 100 and an interior view of the second surface 110-2 of the pocket 100.

In some embodiments, the garment 10 includes a significant degree of elasticity (e.g., stretch) that improves the durability of the tactile device 50, such as when handled by the garment's wearer. Moreover, in some embodiments, the pocket 100 of the present disclosure is integrally formed, at least partially, from the base fabric of the garment 10 rather than as a separate component. For instance, in some embodiments, the first surface 110-1 and the second surface 110-2 form a pocket bag of the garment 10. However, the present disclosure is not limited thereto.

In some embodiments, the first surface 110-1 includes a first distal end portion (e.g., first distal end portion 112-1 of FIG. 2), a first proximal end portion (e.g., first proximal end portion 114-1 of FIG. 2) that runs parallel or approximately parallel to the first distal end portion 112-1 of the first surface 110-1. Furthermore, the first surface 110-1 includes a first upper end portion (e.g., first upper end portion 116-1 of FIG. 2) that connects the first distal end portion 112-1 and the first proximal end portion 114-1 of the first surface 110-1, and a first lower end portion (e.g., first lower end portion 118-1 of FIG. 2) connecting the first distal end portion 112-1 and the first proximal end portion 114-1 of the first surface 110-1. From this configuration, the second surface 110-2 forms a second closed form shape that is a second face of the pocket 100.

Additionally, the second surface 110-2 of the pocket 100 includes a second distal end portion (e.g., second distal end portion 112-2 of FIG. 2) and a second proximal end portion (e.g., second proximal end portion 114-2 of FIG. 2) that runs parallel, or approximately parallel, to the second distal end portion 112-2. Furthermore, the second surface 110-2 includes a second upper end portion (e.g., second upper end portion 116-2 of FIG. 2) that connects the second distal end portion 112-2 and the second proximal end portion 114-2 of the second surface. A second lower end portion (e.g., second lower end portion 118-2 of FIG. 2) connects the second distal end portion 112-2 and the second proximal end portion 114-2 of the second surface 110-2. From this configuration, the second surface 110-2 forms a second closed form shape that is a second face of the pocket 100. In some embodiments, the second closed form shape of the second surface 110-2 is the second as the first closed form shape of the first surface 110-1, such that the pocket 100 is formed with reflectional symmetry about a plane of the pocket 100. However, the present disclosure is not limited thereto. While the exemplary embodiments of FIGS. 1 and 2 illustrate a pocket 100 having a rectangular shape, one of skill in the art will appreciate that other shapes of the pocket 100 are within the scope of the present disclosure, such as pyramidal shaped pockets and the like.

The garment 10 includes a cord (e.g., cord 200 of FIG. 1) of the tactile device 50 that couples the tactile device 50 to the garment 10. Specifically, the cord 200 includes an exterior surface that forms a spine of the tactile device 50. A first end portion of the cord 200 is disposed interposing between the first proximal end portion 114-1 of the first surface 110-1 and the second proximal end portion 114-2 of the second surface 110-2. From this, the first end portion of the cord 200 is coupled to the pocket 100 interposing between the first surface 110-1 and the second surface 110-2, which prevents movement of the first end portion of the cord 200.

In some embodiments, a second end portion of the cord 200 is disposed interposing between the first lower end portion 118-1 of the first surface 110-1 and the second lower end portion 118-2 of the second surface 110-2. In this way, the second end portion of the cord 200 is disposed at a different end portion of the pocket 100 than the first end portion of the cord 200. However, the present disclosure is not limited thereto. For instance, in some embodiments, the second end portion of the cord 200 is disposed interposing between the first proximal end portion 114-1 of the first surface 110-1 and the second proximal end portion 114-2 of the second surface 110-2, such that the first and second end portions of the cord 200 are affixed on a same side of the pocket 100. From either configuration, a first length of the cord 200 is exposed within an interior of the pocket 100, which is configured to accommodate one or more tactile elements 300 and be grasped by a hand of the user. Moreover, the first and second end portions of the cord 200 are coupled to the pocket 100 by interposing between respective portions of the first surface 110-1 and the second surface 110-2. Furthermore, a strength of the cord 200 is increased by having both the first end portion and the second end portion of the cord 200 affixed interposing between the first surface 110-1 and the second surface 110-2 of the pocket 100, which allows a subject to handle the tactile device 50 vigorously and reduces a risk of the tactile device 50 being separated from the garment 10. However, the present disclosure is not limited thereto. For instance, as described supra, the second end portion of the cord 200 is a free end portion that is unrestricted within the pocket 100. By way of example, in some embodiments, the second end portion of the cord 200 includes a knot (e.g., a stopper knot, a monkey's first knot, etc.) and the like, which prevents removal of a plurality of tactile devices (e.g., tactile element 300 of FIG. 4) from the tactile device 50, while also providing a tactual sensation when handled by a user of the garment 10.

In some embodiments, the cord 200 includes an elastic material, allowing for a greater force to be applied to, or through, the cord 200 due to an elasticity of the cord 200. For instance, in some embodiments, the cord 200 is a bungee cord. The bungee cord 200 is formed from either an elastic core (e.g., rubber) surrounded by one or more strands of fabric (e.g., nylon) that form the exterior surface of the bungee cord 200 or the one or more strands (e.g., from about 2 strands to about 30 strands) of fabric with omission of the elastic core. In some alternative embodiments, the cord 200 is made of cotton, wool, jute, leather, polyester, nylon or a blend thereof. As a non-limiting example, in some embodiments, the cord is made of a blend that includes a range of from 85% to 95% nylon by weight and from 5% to 15% spandex by weight.

The garment 10 further includes a plurality of tactile elements (e.g., tactile elements 300 of FIG. 2, tactile element 300-1 of FIG. 4, etc.), which provide a tactual sensation when handled by the subject of the garment 10 (e.g., grasped by a hand of the subject). Each respective tactile element 300 in the plurality of tactile elements 300 includes a through-hole (e.g., through-hole 330 of FIG. 4, through-hole 330 of FIG. 7) configured to receive a portion of the cord 200. By way of the through-hole 330, each respective tactile element 300 is disposed on the cord 200. Specifically, each respective tactile element 300 is disposed circumjacent to the exterior surface of the cord 200. With the cord 200 having at least the first end portion affixed between the first surface 110-1 and the second surface 110-2 of the pocket 100, and the second end portion either affixed between the first surface 110-1 and the second surface 110-2 of the pocket or having the knot, each respective tactile element 300 is prevented from being removed from the garment 10 due to a shape of each respective tactile element 300. In some embodiments, the plurality of tactile elements 300 is between 1 tactile element 300) and 50 tactile elements 300, between 2 tactile elements 300 and 25 tactile elements 300, between 2 tactile elements 300) and 20 tactile elements 300, between 3 tactile elements 300) and 20 tactile elements 300, between 2 tactile elements 300) and 15 tactile elements 300, between 3 tactile elements 300) and 15 tactile elements 300), between 3 tactile elements 300 and 14 tactile elements 300, between 3 tactile elements 300) and 12 tactile elements 300, between 3 tactile elements 300 and 11 tactile elements 300, between 3 tactile elements 300 and 10 tactile elements 300, between 3 tactile elements 300) and 7 tactile elements 300, or a combination thereof. By having more than one tactile element 300, a surface area of the tactile device 50 for improved handling by the user of the garment 10.

The through-hole 330 includes at least a first opening (e.g., first opening 332-1 of FIG. 4, first opening 332-1 of FIG. 6, first opening 332-1 of FIG. 7) and a second opening (e.g., second opening 332-2 of FIG. 4, second opening 332-2 of FIG. 6), allowing the cord 200 to pass through the respective tactile element 300 from a first end portion of the respective tactile element 300 to a second end portion of the respective tactile element 300. In some embodiments, the first opening 332-1 and the second opening 332-2 are formed on opposing end portions of the respective tactile element 300, which provides a straight or substantially straight through-hole 330. Accordingly, the straight or substantially straight through-hole 330) allows for the respective tactile element 300 to rotate axially about the cord 200 with reduced resistance from the exterior surface of the cord 200. However, the present disclosure is not limited thereto. For instance, in some alternative embodiments, the first opening 332-1 is formed on a first face (e.g., first face 700-1 of FIG. 6) of the tactile element 300 and the second opening 332-2 is formed on a second face of the tactile element 300 that is orthogonal or adjacent to the first face 700-1. In some embodiments, the first opening 332-1 is formed on the first face 700-1 of a respective tactile element 300 and the second opening 332-2 is formed on an edge (e.g., second edge 704-2 of FIG. 7) of the respective tactile element 300. In other embodiments, the first opening 332-1 is formed on the first face 700-1 of the respective tactile element 300 and the second opening 332-2 is formed on a vertex (e.g., second vertex 706-2 of FIG. 7) of the respective tactile element 300.

By changing a positioning of the first opening 332-1 and the second opening 332-2 of the through-hole 330, an internal shape of the through-hole 330 is modified to either increase or decrease a resistance of the cord 200 when rotating or traversing the respective tactile element 300 about the cord 200.

Figure 4:
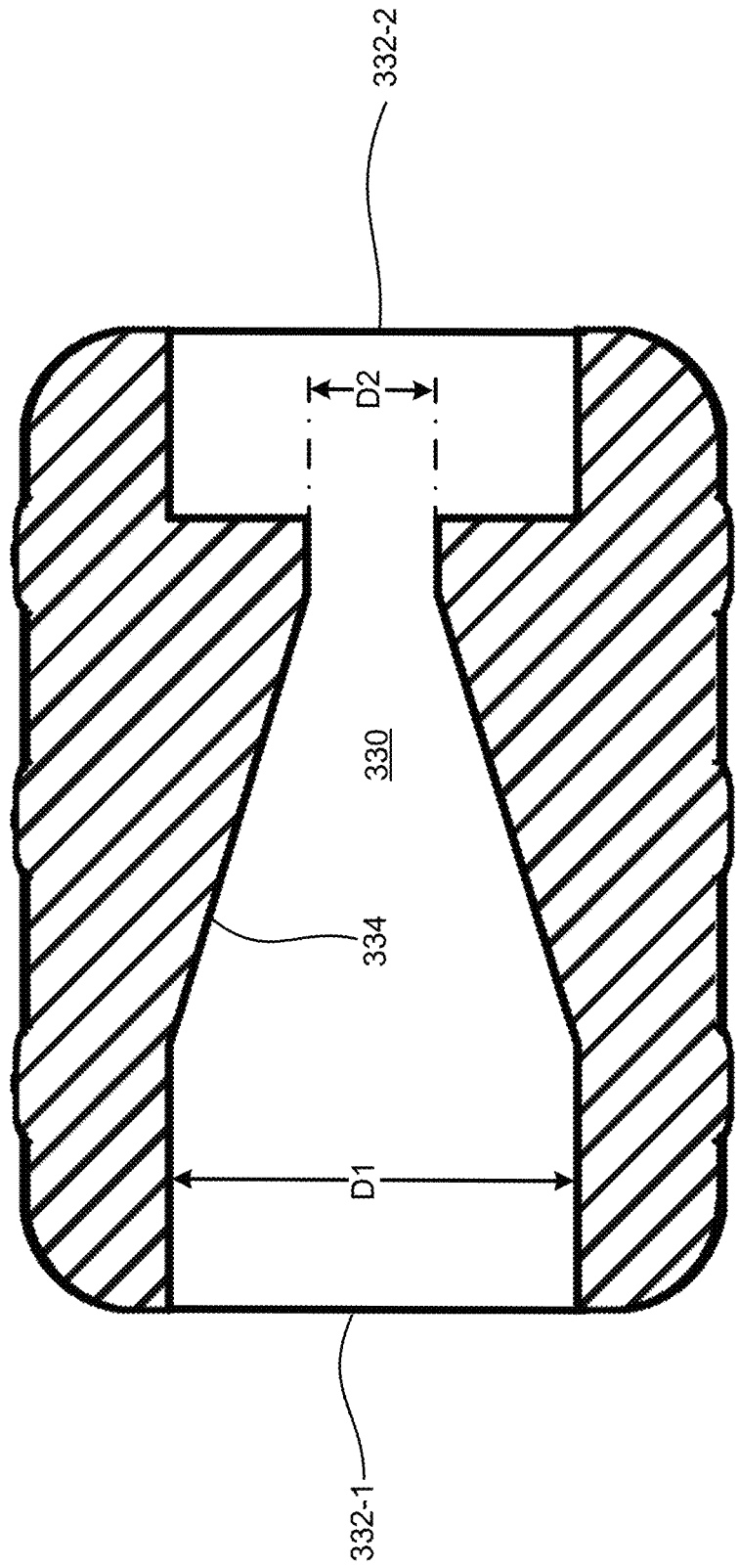
FIG. 4 illustrates a cross-sectional view of a first tactile element, in accordance with an exemplary embodiment of the present disclosure, in which the cross-sectional view is taken along the line B-B of FIG. 3.
Figure 6:
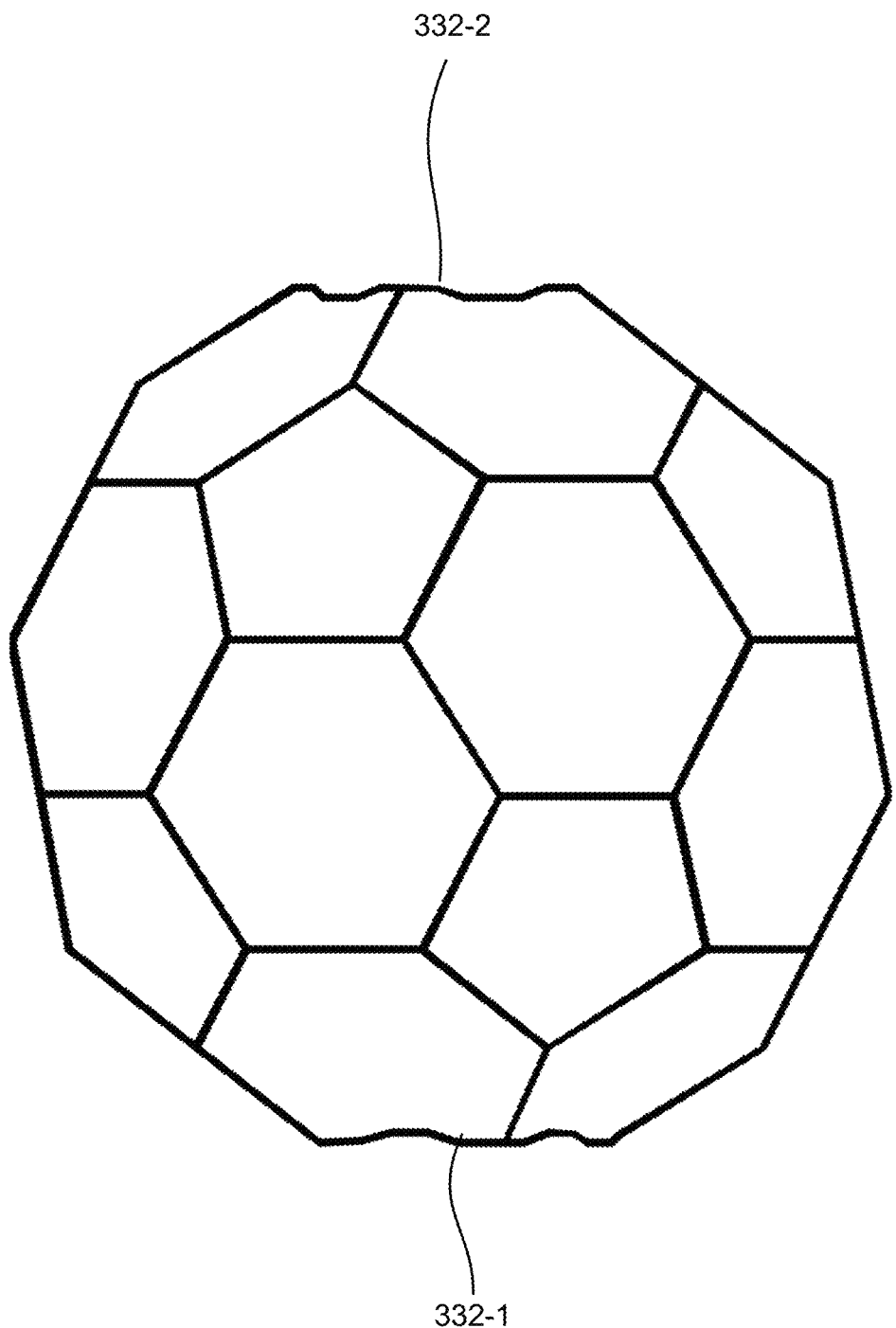
FIG. 6 illustrates a first view of a second tactile element in accordance with an exemplary embodiment of the present disclosure.

In some embodiments, the first opening 332-1 includes a first diameter (e.g., first diameter D1 of FIG. 4, first diameter D1 of FIG. 6, first diameter D1 of FIG. 7, etc.), and the second opening 332-2 includes a second diameter (e.g., D2 of FIG. 4, D2 of FIG. 6, etc.). In some embodiments, the first diameter D1 of the first opening 322-1 is different from the second diameter D2 of the second opening 332-2, which provides for variance when handling the tactile device 50 of the present disclosure. By way of example, in some embodiments, the first diameter D1 of the first opening 332-1 is in a range of from about 0.5 millimeters (mm) to about 4.0 mm, from about 0.5 mm to about 3.5 mm, from about 0.5 mm to about 3.0 mm, from about 1.0 mm to about 3.5 mm, from about 1.0 mm to about 3.0 mm, from about 1.0 mm to about 2.5 mm, or a combination thereof. In some embodiments, the first diameter D1 of the first opening 322-1 is 1.5 mm. In some embodiments, the first diameter D1 of the first opening 332-1 is less than or equal to a fourth diameter of the cord 200, which provides a snug or tight fitting between the first opening 332-1 of the respective tactile element 300 and the exterior surface of the cord 200.

Additionally, in some embodiments, the second diameter D2 of the second opening 332-2 is in a range of from 3.5 mm to about 8 mm, from about 4 mm to about 7.5 mm, from about 4 mm to about 6.5 mm, from about 4.5 mm, to about 6.5 mm, from about 5 mm to about 6.5 mm, from about 5 mm to about 6.0 mm, from about 5.2 mm to about 5.7 mm. In some embodiments, the second diameter D2 of the second opening 322-2 is about 5.5 mm. Furthermore, in some embodiments, the second diameter D2 of the second opening 332-2 is greater than the fourth diameter of the cord 200, which provides a loose fitting (e.g., a large gap) between the exterior surface of the cord 200 and the second opening 332-2 of the respective tactile element 300. Additionally, by having the second opening 332-2 greater than the fourth diameter of the cord 200, the user is provided with a greater freedom to manipulate (e.g., twist, compress, pull, etc.) the respective tactile element 300 about the cord 200. However, the present disclosure is not limited thereto.

Additionally, the cord 200 includes the fourth diameter of the exterior surface. In some embodiments, the fourth diameter of the cord 200 is from about 2 mm to about 10 mm, from about 2 mm to about 7 mm, from about 2 mm to about 6 mm, from about 3 mm to about 6 mm, from about 2 mm to about 5 mm, from about 3 mm to about 5 mm, from about 2 mm to about 4 mm, or a combination thereof. In some embodiments, the fourth diameter of the cord is about 3.18 mm.

In some embodiments, a transition region (e.g., transition region 334 of FIG. 4) is formed that interposes between the first opening 332-1 and the second opening 332-2 of the corresponding through-hole 330. Accordingly, in some such embodiments, the transition region is formed in an interior portion of the respective tactile element 300. In some embodiments, the transition region 332 includes either a step transition from the first diameter D1 of the first opening 332-1 to the second diameter D2 of the second opening 332-20, such that the transition region 332 provides one or more discrete steps from the first diameter D1 to the second diameter D2. In other embodiments, the transition region 334 includes a ramp transition from the first diameter D1 of the first opening 332-1 to the second diameter D2 of the second opening 332-2. In some embodiments, the ramp transition region 334 includes a linear function, a polynomial function, a cubic spline function, and the like that defines an interior surface of the through-hole 330. By way of example, a transition region 334 of FIG. 4 illustrates a linear ramp transition with a constant slope function from the first diameter D1 of the first opening 332-1 to the second diameter D2 of the second opening 332-2. Additionally, in some embodiments, the transition region 334 of the through-hole 330 includes one or more curves, or bends, interposing between the first opening 332-1 and the second opening 332-2. For instance, in some embodiments, the transition region 334 is defined by revolving a continuous, smooth curving about a longitudinal axis of the respective tactile element 300. This smooth curve transition region 334 includes a variety of shapes such as an arc of a circle or a sine function. In some embodiments, the transition region 334 includes a first surface including one or more rounded protrusions that extend, such as a first protrusion that extends towards a longitudinal axis of the respective tactile element 300 and/or a second protrusion that extends away from the longitudinal axis (e.g., an internal protrusion). In some embodiments, the transition region includes a second surface including a bulging inverse curvature, such as a crest on the second surface.

In some embodiments, a maximum deformation of the respective tactile element 300 without a visible (e.g., to the naked eye) loss of structural integrity of the respective tactile element 300 is based, at least in part, on the first diameter D1, the second diameter, a diameter of the transition region 334.

In some embodiments, the plurality of tactile elements 300 includes one or more subsets of tactile elements 300, such as a first subset of tactile elements 300 in the plurality of tactile elements 300 and a second subset of tactile elements 300 in the plurality of tactile elements 300. In some embodiments, the plurality of tactile elements 300 includes at least two tactile element 300, at least three tactile elements 300, at least four tactile elements 300, at least five tactile elements 300, at least six tactile elements 300, at least ten tactile elements 300, at least fifteen tactile elements 300, at least forty tactile elements 300, etc. Accordingly, in some such embodiments, a respective subset in the one or more subsets of tactile elements 300 includes between 1 tactile element 300 and 25 tactile elements 300, between 2 tactile elements 300 and 20 tactile elements 300, between 3 tactile elements 300) and 20 tactile elements 300, between 2 tactile elements 300) and 15 tactile elements 300, between 3 tactile elements 300) and 15 tactile elements 300), between 3 tactile elements 300) and 14 tactile elements 300, between 3 tactile elements 300 and 12 tactile elements 300), between 3 tactile elements 300) and 11 tactile elements 300, between 3 tactile elements 300 and 10 tactile elements 300, between 3 tactile elements 300 and 7 tactile elements 300, or a combination thereof. In some embodiments, each respective tactile element 300 in each respective subset of tactile elements 300 is characterized by a unique shape of the respective subset of tactile elements 300, a unique material of the respective subset of tactile elements, a unique color of the respective subset of tactile elements 300, or a combination thereof. For instance, in some embodiments, each tactile element 300 in a first subset of tactile elements 300 is characterized by a first unique shape (e.g., a toroid), and each tactile element 300 in a second subset of tactile elements 300 is characterized by a second unique shape (e.g., a cuboid). However, the present disclosure is not limited thereto. In this way, each unique subset of tactile elements 300 in the plurality of tactile elements 300 provides a different tactual sensation when handled by a user of the garment 10. From this, variations in arrangements of each tactile element in the plurality of tactile elements 300 based on a corresponding subset of one or more tactile elements 300 provides for patterning of the tactile elements 300. By way of example. FIG. 2 illustrates a tactile device 50 having a plurality of tactile elements 300 including a first subset of tactile elements 300 characterized by a polyhedral shape including a first tactile element 300-1 and a fifth tactile element 300-5, a second subset of tactile elements 300 characterized by a toroid shape including a second tactile element 300-2 and a fourth tactile element 300-4, and a third subset of tactile elements 300 characterized by a prism shape including a third tactile element 300-3. As another non-limiting example, in some embodiments, a respective subset of one or more tactile element 300 includes an asymmetric shape or a shape that is symmetric about an axis of the shape (e.g., a longitudinal axis, etc.). In some embodiments, the respective tactile element 300 includes one or more curved surfaces, such as one or more convex surfaces and/or one or more concave surfaces (e.g., concave dimples). Moreover, in some embodiments, the respective tactile element includes one or more edges that connect one or more surfaces of the respective tactile element 300. In some embodiments, a respective edge in the one or more edges includes a chamfer edge or rounded edge (e.g., fillet). However, the present disclosure is not limited thereto. Furthermore, in some embodiments, Furthermore, in some embodiments, a respective subset of tactile elements 300 includes a unique color (e.g., a first subset of tactile elements 300 includes a red color, a second subset of tactile elements 300 includes a silver color, etc.).

Figure 7:
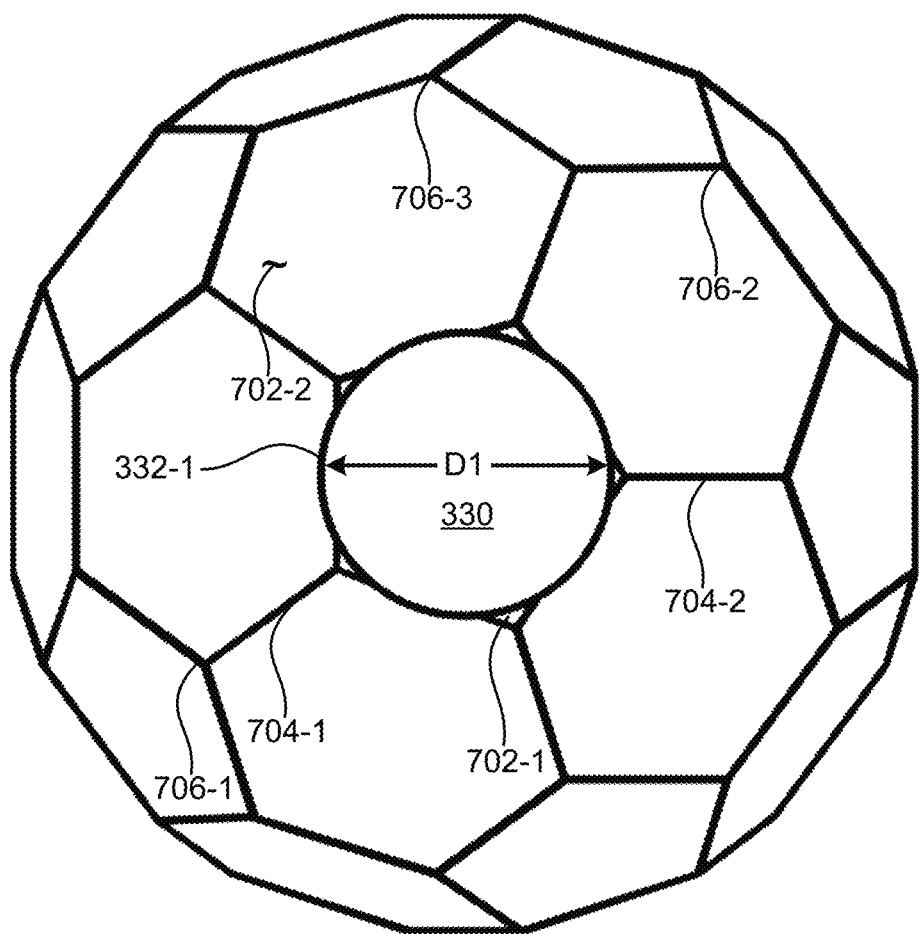
FIG. 7 illustrates a second view of a second tactile element in accordance with an exemplary embodiment of the present disclosure.

Referring briefly to FIG. 6 and FIG. 7, in some embodiments, the first unique shape of a respective tactile element 300 is sphere or spheroid shaped. However, the present disclosure is not limited thereto. In some embodiments, the first unique shape is a polyhedron. The polyhedron shape includes a regular polyhedron that is isohedral (e.g., an isohedron such as a cube or a dipyramid) or a quasi-regular polyhedron that is isogonal. In some embodiments, the first unique shape of the respective tactile element 300 is a Johnson solid. Additional details and information regarding Johnson solids can be found at Johnson, Norman, 1966, "Convex Polyhedra With Regular faces," Canadian Journal of Mathematics, 18, pg. 169, which is hereby incorporated by reference in its entirety. In some embodiments, one or more faces 702 of the polyhedron is a curved face, such as a respective face 702 having convex and/or concave curvature or a round polyhedron. For instance, in some embodiments, the first unique shape is a toroidal polyhedron (e.g., second tactile element 300-2 of FIG. 2). In some embodiments, the first unique shape is spheroid with a plurality of dimples. In some embodiments, each dimple in the plurality of dimples includes a third diameter. In some embodiments, the third diameter of the dimples is greater than the fourth diameter of the cord 200. By utilizing the plurality of dimples, or by having one or more faces 700 with convex or concave surface, a tactual sensation provided when handling the edges 704 of the respective tactile element 300 are enhanced based on a sudden change in displacement of the faces 702 of the respective tactile element 300. However, the present disclosure is not limited thereto. For instance, in some embodiments, the first unique shape is a truncated polyhedron, as opposed to having the plurality of dimples. Additional details and information regarding the unique shape of a respective tactile element 300 can be found at Kotschick, Dieter, 2006, "The Topology and Combinatorics of Soccer Balls: When Mathematicians Think About Soccer Balls, the Number of Possible Designs Quickly Multiplies," American Scientist, 94 (4), pg. 350, which is hereby incorporated by reference in its entirety.

In some embodiments, the first unique shape of a respective tactile element 300 is a toroidal shape. By way of example, a fourth tactile element 300-4 of FIG. 2 illustrates a toroidal shaped tactile element 300. In some embodiments, the first unique shape is prism shape, such as a cone, a rectangular prism, a sphere, a cylinder, a cube, a triangular prism, a pentagonal pyramid, an octagonal prism, and the like. As such, the prism shape of the respective tactile element 300 includes a first base. In some embodiments, the first opening 332-1 of the corresponding through-hole 330 of the respective tactile element 300 is formed on the first base. Moreover, in some embodiments, a second base of the prism includes the second opening 332-2 of the corresponding through-hole 330 of the respective tactile element 300. As such, a plurality of surface faces 702 of the prism interposes between the first base and the second base. However, the present disclosure is not limited thereto. For instance, in some embodiments, the second opening 332-2 is formed on a respective face 702 of the prism and the first opening 332-1 is formed on the first base of the prism.

Figure 3:
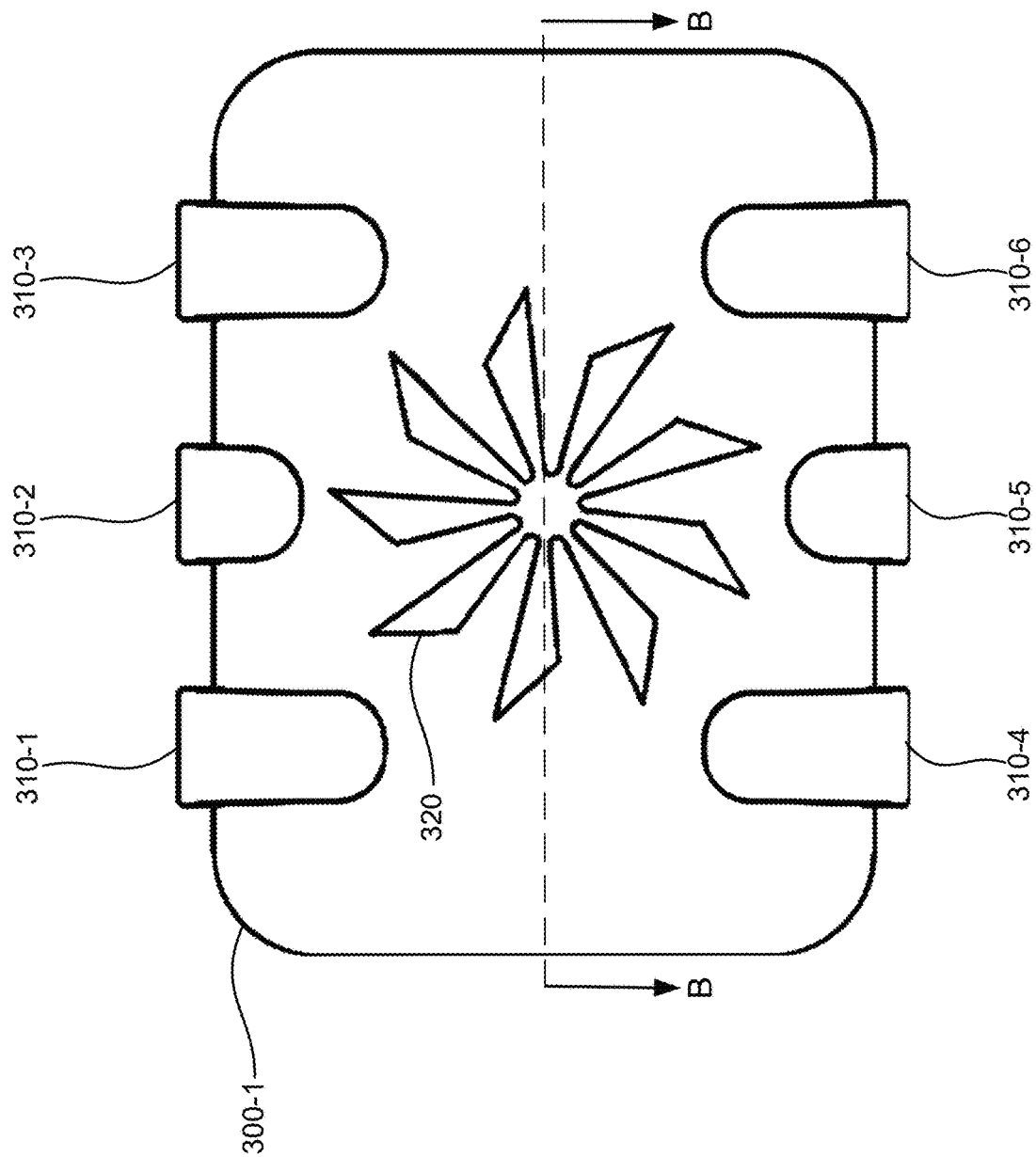
FIG. 3 illustrates a first view of a first tactile element, in accordance with an exemplary embodiment of the present disclosure.
Figure 5:
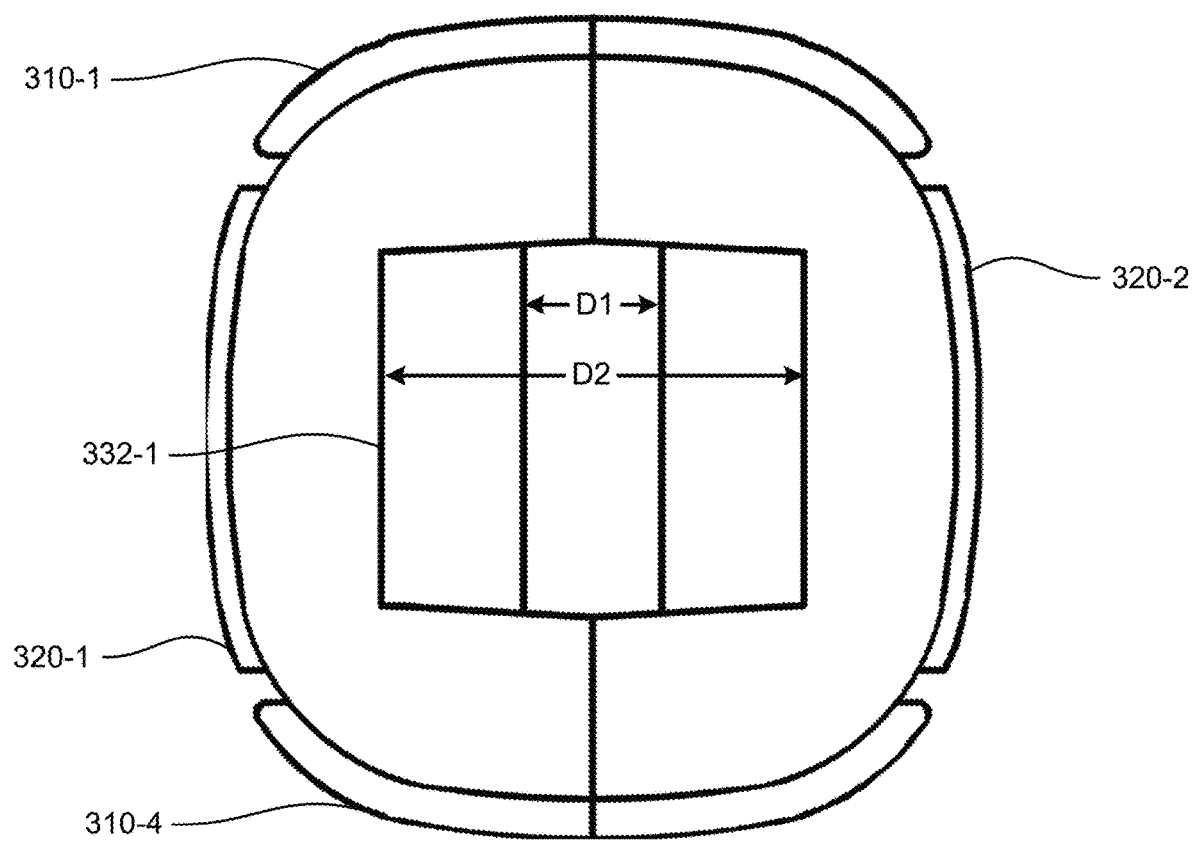
FIG. 5 illustrates a second view of a first tactile element in accordance with an exemplary embodiment of the present disclosure.

In some embodiments, the plurality of surface faces 702 include a first subset of faces 702 in the plurality of surface faces 702. Each respective face 702 in the first subset of faces 702 includes one or more protrusions of a first shape (e.g., protrusions 310 of FIG. 3, protrusion 320-2 of FIG. 5). For instance, in some embodiments, the one or more protrusions 310 include a ribbed shape of FIG. 3. In some embodiments, the plurality of surface faces 702 include a second subset of faces 702 in the plurality of surface faces 702. Each respective face 702 in the second subset of faces includes one or more protrusions of a second shape, such as protrusions 320-2 of FIG. 3. In some embodiments, the one or more protrusions 310, 320 is utilized to increase a surface area of the respective tactile element 300, which provides an enhanced tactual sensation when handled by a user. Additionally, in some embodiments, the one or more protrusions 310, 320 allow for surface differentiation through decorations (e.g., emblems), materials, colors, textures, and the like. In some embodiments, the one or more protrusions extend from a respective face 702 by a height between 0.01 cm to 0.5, between 0.1 cm to 0.5 cm, between 0.2 cm to 0.4 cm, between 0.25 cm to 0.3 cm, or a combination thereof.

In some embodiments, a first face 702-1 in the first subset of faces 702 is parallel to a second face 702-2 in the first subset of faces 702, and a third face 702-3 in the second subset of faces is parallel to a fourth face in the second subset of faces.

In some embodiments, the one or more subsets of tactile elements 300 is a plurality of tactile elements, each tactile element 300 in a first subset of tactile elements in the plurality of tactile elements is characterized by a spheroid shape. Moreover, each tactile element in a second subset of tactile elements in the plurality of tactile elements is characterized by a toroidal shape. Furthermore, each tactile element in a third subset of tactile elements in the plurality of tactile elements 300 by a prism shape includes a first base including a first opening of a corresponding through-hole of the respective tactile element, a second base including a second opening of the corresponding through-hole of the respective tactile element, and a plurality of surface faces interposing between the first base and the second base.

In some embodiments, a respective tactile element 300 has a volume in a range from about 0.5 cubic centimeters ($cm^3$) to about 10 $cm^3$, from about 1 $cm^3$ to about 10 $cm^3$, from about 1 $cm^3$ to about 8 $cm^3$, from about 1 $cm^3$ to about 7 $cm^3$, from about 1 $cm^3$ to about 6 $cm^3$, from about 1.5 $cm^3$ to about 6.5 $cm^3$, from about 2 $cm^3$ to about 6 $cm^3$, from about 2.5 $cm^3$ to about 5 $cm^3$, from about 1.5 $cm^3$ to about 3 $cm^3$, from about 2 $cm^3$ to about 4 $cm^3$, or a combination thereof.

In some embodiments, a characteristic dimension (e.g., a characteristic width, a characteristic length) of the respective tactile element 300 is in a range from about 0.2 cm to about 5 cm, from about 0.5 cm to about 3 cm, from about 0.75 cm to about 2.5 cm, from about 0.8 cm to about 1.5 cm, from about 0.5 cm to about 3.16 cm, from about 1 cm to about 2 cm, or a combination thereof.

In some embodiments, the first subset of tactile elements 300 includes a first tactile element and a second tactile element in the plurality of tactile elements, the second subset of tactile elements includes a third tactile element and a fourth tactile in the plurality of tactile elements, and the third subset of tactile elements includes a fifth tactile element in the plurality of tactile elements. In some embodiments, the fifth tactile element is disposed on the cord interposing between the third tactile element and the fourth tactile element. In some embodiments, each tactile element 300 in the first subset of tactile elements in plurality of tactile elements is adjacent to a respective tactile element in the second subset of tactile elements in plurality tactile elements and/or the third subset of tactile elements in the plurality of tactile elements. Said otherwise, in some such embodiments, each tactile element 300) in the first subset of tactile elements is not adjacent to another tactile element 300 in the first subset of tactile elements. However, the present disclosure is not limited thereto.

In some embodiments, each tactile element 300 in the plurality of tactile elements 300 includes thermoplastic rubber, which provides a durable, flexible tactile element 300, such as a material susceptible to repeated elastic deformation. Thermoplastic rubbers include thermoplastic polyolefinelastomer, a thermoplastic vulcanization, a thermoplastic polyurethane, a thermoplastic polyester, or a thermoplastic polyamide.

In some embodiments, a respective tactile element 300 has a Shore A hardness in a range from about 10 to about 20, from about 15 to about 20, from about 15 to about 25, from about 20 to about 25, from about 20 to about 30, from about 25 to about 30, from about 25 to about 35, from about 30) to about 40, from about 35 to about 40), from about 35 to about 45, from about 40) to about 45, from about 40) to about 50, from about 45 to about 50, from about 45 from about 55, from about 50 to about 55, from about 50) to about 60, from about 55 to about 65, from about 65 to about 80, or a combination thereof. In some embodiments, the respective tactile element 300 has a Shore 00 hardness in a range from about 7 to about 12, from about 10 to about 15, from about 13 to about 20, from about 17 to about 22, from about 20) to about 25, from about 23 to about 30, from about 27 to about 32, from about 30) to about 35, from about 33 to about 40), from about 37 to about 42, from about 40) to about 45, from about 43 to about 50), or a combination thereof. Accordingly, in some such embodiments, the hardness of the respective tactile element 300 allows the user to deform the respective tactile element 300 using their hand alone. However, the present disclosure is not limited thereto. In some embodiments, each tactile element in the first subset of tactile elements includes a first hardness (e.g., Shore A hardness of about 20) and each tactile element in the second subset of tactile elements includes a second hardness different than the first hardness (e.g., Shore A hardness of about 50). However, the present disclosure is not limited thereto.

A plurality of seams (e.g., first seam 120, second seam 122, third seam 124, etc.) are formed to affix at least the first surface 110-1 and the second surface 110-2 of the pocket 100. Furthermore, in some embodiments, at least one seam in the plurality of seams further affixes the cord 200 to the pocket 100 of the garment 10, such as the first seam 120 and the second seam 122 of FIG. 2. For instance, in some embodiment, the first proximal end portion 114-1 of the first surface 110-1 and the second proximal portion of the second surface 110-2 are affixed (e.g., bonded, fused, sewn, welded, etc.) by the first seam (e.g., first seam 120 of FIG. 2). Specifically, the first seam 120 affixes the first proximal end portion 114-1 of the first surface 110-1, the second proximal end portion 114-2 of the second surface 110-2, and the first end portion of the cord 200. In some embodiments, the first seam 120 further affixes a fastening mechanism (e.g., zipper fastening mechanism 500 of FIG. 2) of the garment 10. By having the first seam 120 affix both the first end portion of the cord 200 and the fastening mechanism 500 of the garment, a strength of the first seam 120 increases. From this, a user of the garment 10 having the tactile device 50 can handle the tactile device 50 with greater force applied to the tactile device 50 and the seams of the garment 10.

Additionally, a second seam (e.g., second seam 122 of FIG. 2) affixes the first lower end portion 118-1 of the first surface 110-1, the second lower end portion 118-2 of the second surface 110-2, and the second end portion of the cord 200. From this, the cord 200 is fixedly disposed within the pocket 100 by at least the second seam 122. However, the present disclosure is not limited thereto. For instance, in some embodiments, a third seam (e.g., third seam 124 of FIG. 2) is a hem of the garment 10. By way of example, the third seam 124 of FIG. 2 illustrates a hem of a waist portion of a jacket garment 10. Furthermore, in some embodiments, the first seam 120 and/or the second seam 122 is a hem of the garment 10. By affixing the cord 200 through the hem seam (e.g., third seam 124) a durability of the tactile device 50 increases. Additionally, in some embodiments, one or more bar tacks 126 is used to further affix the cord 200 and the garment 10, such as a first bar tack 126-1 to affix the first end portion of the cord 200 to the garment 10. In some embodiments, the one or more bar tacks 126 overlap a seam (e.g., first seam 120) of the garment 10.

In some embodiments, the garment 10 further includes a fourth seam (e.g., fourth seam 125 of FIG. 2) affixing the first upper end portion 116-1 of the first surface 110-1 and the second upper end portion 116-2 of the second surface 110-2 of the pocket 100. From this, an aperture (e.g., aperture 400 of FIG. 2) forms for receiving a hand of the user. This aperture 400 is defined by at least the first upper end portion 116-1 of the first surface 110-1 and the second upper end portion 116-2 of the second surface 110-2, allowing the user to insert and/or retract a hand through the aperture 400. Furthermore, in some embodiments, a distal end portion of the first seam 120 is near to the lower end portion of the garment 10, such that the aperture 400 forms a slope from the first seam 120 to the fourth seam 125. In some embodiments, this slope of the aperture 400 is configured such, even though a characteristic width of the aperture 400 is less than a width of a hand of the subject, the slope provides an increased area of the aperture 400 for receiving the hand of the subject.

In some embodiments, a respective seam in the plurality of seams (e.g., first seam 120 of FIG. 2, second seam 122 of FIG. 2, third seam 124 of FIG. 2, fourth seam 125 of FIG. 2, etc.) affixes components of the garment 10 by sewing a corresponding line of stitches that extend a length of the respective seam 120, 122, 124, 125. For instance, in some embodiments, a respective seam 120, 122, 124, 125 is a single-need stitch, a lock stitch, a chain stitch, a bar tack, or the like. In some embodiments, the respective seam 120, 122, 124, 125 the garment 10 is formed using an International Organization for Standardization (IOS, 1991) class 100 single-thread chain stitch, class 200 hand stitch, class 300 lockstitch, class 400 multi-thread stitch, class 500 overedge/overlock stitch, or class 600 covering chain stitch. In some embodiments, the first seam 120 or the second seam 122 of the garment 10 is a U.S. Standard SS superimposed seam, LS lapped seam, BS bound seam, or FS flat seam. However, the present disclosure is not limited thereto. Additional details and information regarding the IOS stitch classification and terminology is described in LST ISO 4915, 2002, "Textiles, Stitch Types: Classification and Terminology," print, which is hereby incorporated by reference in its entirety. Moreover, in some embodiments, a respective seam in the plurality of seams 60 is a United States Standard superimposed seam (SS), lapped seam (LS), bound seam (BS), or flat seam (FS). Additional details and information regarding the United Stated Standard classification is described in United States Bureau of Standards et al., 1926, "United States Government Master Specification for Stitches, Seams, and Stitching: Federal Specifications Board Specification No. 384," Washington: Govt., print, which is hereby incorporated by reference in its entirety.

In some embodiments, the first seam 120 is characterized by a first seam strength in between 10 kilograms-force (kgf) and 35 kgf. In some embodiments, the second seam is characterized by a second seam strength between 10 kgf to 35 kgf. Additional details and information regarding a strength of a seam can be found at Rostam et al., 2014, "Seam Slippage and Seam Strength Behavior of Elastic Woven Fabrics Under Static Loading." Indian Journal of Fiber and Textile Research, 39 (3), pg. 221: Midha et al., 2011, "An Approach to Seam Strength Prediction Using Residual Thread Strength," Research Journal of Textile and Apparel, 15 (3), pg. 75, each of which is hereby incorporated by reference in its entirety.

In some embodiments, a first length of the cord 200 that is exposed in the pocket 100 by the first seam 120 and the second seam 122 is from about 0.5 inches to about 6 inches, from about 1 inch to about 6 inches, from about 1 inch to about 5 inches, from about 1 inch to about 4 inches, from about 2 inches to about 5 inches, from about 2 inches to about 4 inches, from about 1 inch to about 3.5 inches, from about 1.5 inches to about 3.5 inches, from about 2 inches to about 3.5 inches, from about 1.5 inches to about 3 inches, from about 2 inches to about 3 inches, from about 1.5 inches to about 2.5 inches, from about 2 inches to about 2.5 inches, or a combination thereof. In some embodiments, the first length of the cord 200 that is exposed in the pocket 100 is 2.5 inches.

In some embodiments, a setting length (LS), which is a length of a straight line formed between the first end portion and the second end portion of the cord 200. For instance, in some embodiments, the setting length is the length of the straight line from the first bar tack 126-1 to the second bar tack 126-2 of the garment 10. In alternative embodiments, the setting length is the length of the straight line from the first seam 120 to the second seam 122. In some embodiments, the setting length of the cord 200 is from about 1 inch to about 5 inches, from about 1 inch to about 4 inches, from about 2 inches to about 5 inches, from about 2 inches to about 4 inches, from about 1 inch to about 3.5 inches, from about 1.5 inches to about 3.5 inches, from about 2 inches to about 3.5 inches, from about 1.5 inches to about 3 inches, from about 2 inches to about 3 inches, from about 1.5 inches to about 2.5 inches, from about 2 inches to about 2.5 inches, or a combination thereof. In some embodiments, the setting length of the cord 200 is 2.25 inches. By changing the setting length of the cord 200, a tension of the cord 200 and/or the first length of the cord 200 is configured for the tactile device 50.

In some embodiments, a second length that is a sum of each length of each respective tactile element 300 in the plurality of tactile elements 300 is in a range of from about 0.2 inches to about 4 inches, from about from 0.5 inches to about 4 inches, from about 1 inch to about 3.5 inches, from about 1 inch to about 3 inches, from about 1 inch to about 2.5 inches, from about 1.5 inches to about 2.5 inches, from about 1.5 inches to about 2.0 inches, from 1.5 inches to about 1.9 inches, or a combination thereof. In some embodiments, the second that is the sum of each length of each respective tactile element 300 in the plurality of tactile elements 300 is 1.75 inches. As such, a range of movement of each respective tactile element 300 in the plurality of tactile elements 300 is depends at least on a ratio between the second length of the plurality of tactile elements 300 and the first length of the cord 200.

REFERENCES CITED

All referenced cited herein are incorporated herein by reference in their entirety and for all purposes to the same extent as if each individual publication or patent or patent application was specifically and individually indicated to be incorporated by reference in its entirety for all purposes.

What is claimed is:

1. A garment comprising a pocket, wherein the pocket comprises:
   a first surface comprising:
      a first distal end portion,
      a first proximal end portion running parallel to the first distal end portion, wherein the first distal end portion is away from a central line of the garment and the first proximal end portion is closer to the central line of the garment, wherein the central line of the garment bisects a front of the garment to a left portion and a right portion,
      a first upper end portion connecting the first distal end portion and the first proximal end portion, wherein the first upper end portion is perpendicular to the central line of the garment, and
      a first lower end portion connecting the first distal end portion and the first proximal end portion, wherein the first lower end portion is perpendicular to the central line of the garment;
   a second surface opposing the first surface, the second surface comprising:
      a second distal end portion,
      a second proximal end portion running parallel to the second distal end portion, wherein the second distal end portion is away from the central line of the garment and the second proximal end portion is closer to the central line of the garment,
      a second upper end portion connecting the second distal end portion and the second proximal end portion, wherein the second upper end portion is perpendicular to the central line of the garment, and
      a second lower end portion connecting the second distal end portion and the second proximal end portion, wherein the second lower end portion is perpendicular to the central line of the garment;
   a cord comprising:
      an exterior surface,
      a first terminal end portion disposed interposing between the first proximal end portion and the second proximal end portion, and
      a second terminal end portion disposed interposing between the first lower end portion and the second lower end portion;
   a plurality of tactile elements, wherein each respective tactile element in the plurality of tactile elements comprises a through-hole and is disposed on the cord circumjacent to the exterior surface of the cord;
   a first seam affixing the first proximal end portion, the second proximal end portion, and the first terminal end portion of the cord; and
   a second seam affixing the first lower end portion, the second lower end portion, and the second terminal end portion of the cord, thereby fixedly disposing the cord within the pocket.

2. The garment of claim 1, further comprising a fourth seam affixing the first upper end portion and the second upper end portion, thereby forming an aperture for receiving a hand of a subject.

3. The garment of claim 1, wherein:
   the first seam is characterized by a first seam strength in between 20 kilograms-force (kgf) and 35 kgf, and
   the second seam is characterized by a second seam strength in between 15 kgf to 30 kgf.

4. The garment of claim 1, wherein the plurality of tactile elements comprises:
   one or more subsets of tactile elements.

5. The garment of claim 4, wherein:
   the one or more subsets of tactile elements each comprises at least two tactile elements,
   each tactile element in a first subset of tactile elements in the one or more subsets of tactile elements is characterized by a first shape, and
   each tactile element in a second subset of tactile elements in the one or more subsets of tactile elements is characterized by a second shape different from the first shape.

6. The garment of claim 5, wherein the first shape is a toroidal shape.

7. The garment of claim 5, wherein the first shape is prism shape comprising:
   a first base comprising a first opening of the through-hole of one of the tactile elements in the first subset of tactile elements, a second base comprising a second opening of the through-hole of the one of the tactile elements in the first subset of tactile elements, and a plurality of surface faces interposing between the first base and the second base.

8. The garment of claim 7, wherein the plurality of surface faces comprises:
   a first subset of faces in the plurality of surface faces, wherein each respective face in the first subset of faces comprises one or more protrusions of a third shape, and
   a second subset of faces in the plurality of surface faces, wherein each respective face in the second subset of faces comprises one or more protrusions of a fourth shape.

9. The garment of claim 8, wherein:
a first face in the first subset of faces is parallel to a second face in the first subset of faces, and
a third face in the second subset of faces is parallel to a fourth face in the second subset of faces.

10. The garment of claim 7, wherein:
a first diameter of the first opening is in a range of from 1.5 millimeters (mm) to 2.0 mm, and
a second diameter of the second opening is in a range of from 5.2 mm to 5.7 mm.

11. The garment of claim 10, wherein, a transition region interposing between the first opening and the second opening of the through-hole of the one of the tactile elements in the first subset of tactile elements comprises either:
a step transition from the first diameter of the first opening to the second diameter of the second opening, or
a ramp transition from the first diameter of the first opening to the second diameter of the second opening.

12. The garment of claim 5, wherein the first shape is spheroid shaped.

13. The garment of claim 5, wherein the first shape is spheroid with a plurality of dimples.

14. The garment of claim 13, wherein each dimple in the plurality of dimples comprises a third diameter.

15. The garment of claim 4,
wherein the one or more subsets of tactile elements each comprises at least three tactile elements,
each tactile element in a first subset of tactile elements in the one or more subsets of tactile elements is characterized by a spheroid shape;
each tactile element in a second subset of tactile elements in the one or more subsets of tactile elements is characterized by a toroidal shape; and
each tactile element in a third subset of tactile elements in the one or more subsets of tactile elements is characterized by a prism shape comprising:
a first base comprising a first opening of the through-hole of each tactile element in the third subset of tactile elements,
a second base comprising a second opening of the through-hole of each tactile element in the third subset of tactile elements, and a plurality of surface faces interposing between the first base and the second base.

16. The garment of claim 15, wherein:
the first subset of tactile elements comprises a first tactile element and a second tactile element in the plurality of tactile elements,
the second subset of tactile elements comprises a third tactile element and a fourth tactile in the plurality of tactile elements, and
the third subset of tactile elements comprises a fifth tactile element in the plurality of tactile elements.

17. The garment of claim 16, wherein the fifth tactile element is disposed on the cord interposing between the third tactile element and the fourth tactile element.

18. The garment of claim 1, wherein each tactile element in the plurality of tactile elements comprises thermoplastic rubber.

19. The garment of claim 1, wherein the plurality of tactile elements is between 3 tactile elements and 11 tactile elements.

20. The garment of claim 1, wherein the cord is a bungee cord.

21. The garment of claim 1, wherein the cord is made of cotton, wool, jute, leather, polyester, nylon or a blend thereof.

22. The garment of claim 1, wherein the first seam or the second seam is formed using an International Organization for Standardization (IOS, 1991) class 100 single-thread chain stitch, class 200 hand stitch, class 300 lockstitch, class 400 multi-thread stitch, class 500 overedge/overlock stitch, or class 600 covering chain stitch.

23. The garment of claim 1, wherein the first seam or the second seam is a United States Standard superimposed seam (SS), lapped seam (LS), bound seam (BS), or flat seam (FS).

24. The garment of claim 1, wherein:
a first length of the cord exposed in the pocket by the first seam and the second seam is between 2 inches and 3 inches, and
a second length that is a sum of each length of each respective tactile element in the plurality of tactile elements is in a range of from 1.5 inches to 1.9 inches.

25. A garment comprising a pocket, wherein the pocket comprises:
a first surface comprising:
a first distal end portion,
a first proximal end portion running parallel to the first distal end portion,
a first upper end portion connecting the first distal end portion and the first proximal end portion, and
a first lower end portion connecting the first distal end portion and the first proximal end portion;
a second surface opposing the first surface, the second surface comprising:
a second distal end portion,
a second proximal end portion running parallel to the second distal end portion,
a second upper end portion connecting the second distal end portion and the second proximal end portion, and
a second lower end portion connecting the second distal end portion and the second proximal end portion;
a cord comprising:
an exterior surface,
a first terminal end portion disposed interposing between the first proximal end portion and the second proximal end portion, and
a second terminal end portion disposed interposing between the first lower end portion and the second lower end portion;
a plurality of tactile elements, wherein each respective tactile element in the plurality of tactile elements comprises a through-hole and is disposed on the cord circumjacent to the exterior surface of the cord;
a first seam affixing the first proximal end portion, the second proximal end portion, and the first terminal end portion of the cord;
a second seam affixing the first lower end portion, the second lower end portion, and the second terminal end portion of the cord, thereby fixedly disposing the cord within the pocket;
a third seam affixing the first upper end portion and the second upper end portion; and
an aperture for receiving a hand of a subject,
wherein the first, second and third seams are on three sides of the pocket, with the first seam connected to each of the second and third seams.

* * * * *